United States Patent [19]

Panster et al.

[11] 4,287,094

[45] Sep. 1, 1981

[54] MONOMERIC, POLYMERIC AND CARRIER-FIXED RHODIUM COMPLEX COMPOUNDS, PROCESS FOR THEIR PRODUCTION AND THEIR USE AS CATALYSTS

[75] Inventors: Peter Panster, Hanau; Wolfgang Buder, Rodenbach; Peter Kleinschmit, Hanau, all of Fed. Rep. of Germany

[73] Assignee: Deutsche Gold- und Silber-Scheideanstalt vormals Roessler, Frankfurt am Main, Fed. Rep. of Germany

[21] Appl. No.: 63,291

[22] Filed: Aug. 2, 1979

[30] Foreign Application Priority Data

Aug. 8, 1978 [DE] Fed. Rep. of Germany ....... 2834691

[51] Int. Cl.$^3$ .......................... C07F 15/00; B01J 31/12
[52] U.S. Cl. ........................... 252/431 R; 260/429 R; 260/429 J
[58] Field of Search ................ 260/429 R; 252/431 R

[56] References Cited

U.S. PATENT DOCUMENTS 4,005,046  1/1977  Chandra et al. ................. 252/431 R Primary Examiner—Helen M. S. Sneed
Attorney, Agent, or Firm—Beveridge, DeGrandi & Kline

[57] ABSTRACT

The invention relates to coordination compounds of rhodium with silicon-substitued dialkyl or diaryl sulfide groups as ligands in monomeric, polymeric or carrier-fixed forms. The substance can be used as catalysts.

32 Claims, No Drawings

MONOMERIC, POLYMERIC AND CARRIER-FIXED RHODIUM COMPLEX COMPOUNDS, PROCESS FOR THEIR PRODUCTION AND THEIR USE AS CATALYSTS

BACKGROUND OF THE INVENTION

The invention relates to coordination compounds of rhodium with silicon-substituted dialkyl or diaryl sulfide groups as ligands in monomeric, polymeric or carrier-fixed form, a process for their production and the use of these substances as catalysts.

Sulfide group-containing rhodium compounds have been known for some time (J.C.S. Dalton 1973, 116; J. Prakt. Chem. 315, 106 1973). In the German OS No. 24 05 274, rhodium complexes of trivalent rhodium with ligands (SR'R'') have been described which for example, correspond to the formula:

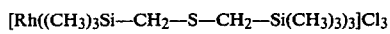

[Rh((CH$_3$)$_3$Si—CH$_2$—S—CH$_2$—Si(CH$_3$)$_3$)$_3$]Cl$_3$

They are to be used as homogeneous catalysts for hydrosilylation reactions. The bivalent sulphur of the ligand is symmetrically bound with a trimethylsilyl group always by way of a methylene group; the valencies of the two silicon atoms are therefore saturated with non-functional; i.e. inert, therefore for example, hydrolysis-resistant groups. Consequently, such compounds may be used as catalysts only in a homogeneous phase.

In the German OS No. 24 53 229 complex compounds of trivalent rhodium have also been proposed in which according to

[RhL$_3$X$_3$]

sulfide ligands with for example, a composition of

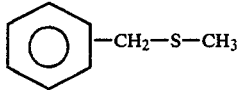

are contained. These compounds are to be used for hydroformylation reactions. They are also used in the homogeneous phase.

One disadvantage in the case of employing these known substances for catalytic purposes is to be seen in the fact, that their separation from components of the reaction mixture and thus also their recapture is cumbersome and expensive. Moreover, the losses occurring thereby of costly noble metals represents a not insignificant cost factor in case of the technical execution of corresponding processes of catalysis.

Finally, in the German OS No. 25 50 660, inorganic catalyst carriers, surface-modified with sulfur-containing, organo substituted silyl groups, such as SiO$_2$, are described, which are coordinatively combined by way of sulfur atoms into a complex of platinum or rhodium. For their production for example, a compound of the formula:

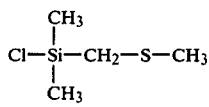

is reacted with surface silanol of the carrier material, so that formally the following structure is achieved:

Carrier—O—Si(CH$_3$)$_2$—CH$_2$—S—CH$_3$

The carrier modified in this way is then reacted with a compound of platinum or rhodium. According to a variation the sulfur containing silane may also first be reacted with a platinum or rhodium compound and the complex obtained may then be reacted with the carrier. The catalyst modified carriers are to be useable for hydroformylation, oligomerization or hydrosilylation reaction. Their main characteristic consists in the fact that the ligand carrying the catalytically active metal is bound to the carrier always only by way of a single silicon atom via oxygen bridges. The radicals not bound to the carrier, attached on the sulfur do not contribute to the fixation.

Now new heterogenizable complex compounds of rhodium have been found which are characterized in that at least one sulfide of the general formula (1):

$$R^1{}_{3-x}(R^2O)_x Si—R^3—S—R^4—Si(OR^5)_y R^6{}_{3-y} \qquad (1)$$

is bound coordinatively to the central atom, its possibly still free places of coordination are occupied by a carbon monoxide, an olefin, amine, phosphin or nitrile and a required charge equalization with chloride, bromide or iodide ion, acetate, trifluoroacetate or trifluoro-propionate, possibly with complete or partial replacement of such anions by hydride ion, is accomplished, wherein the formula 1

$R^1$ and $R^6$ may stand for: a straight-chain or branched alkyl group with 1 to 5 C-atoms, a cycloalkyl radical with 5 to 8 C-atoms, the benzyl or phenyl radical, possibly substituted with methyl, ethyl, propyl, methoxy, ethoxy groups, NO$_2$-groups, halide or cyanide substituted as well as for chloride or bromide, $R^2$ and $R^5$ may stand for a straight chain or branched alkyl group with 1 to 5 C-atoms, a cycloalkyl group with 5 to 8 C-atoms, the possibly substituted phenyl or benzyl group or the 2-methoxy or 2-ethoxy-ethyl group, whereby $R^2$ and $R^5$ may have the same or different meaning, $R^3$ and $R^4$ may stand for a straight chain or branched alkylene group with 1 to 10 C-atoms, for a phenylene or cycloalkylene group with 5 to 8 C-atoms, possibly substituted with a methyl, ethyl, propyl or iso-propylene group; and for units of the type

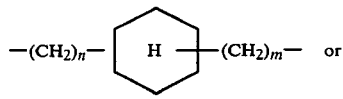   or

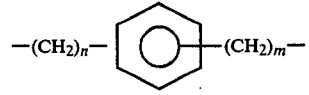

whereby n or m may be a number from 0 to 5 and the ring-positioned H-atoms may be partially replaced by halogen, especially by F, Cl, Br, the cyanide group, and $R^3$ and $R^4$ have the same or a different meaning and whereby x and y may be 1, 2 or 3, but also 0; namely, whenever $R^1$ or $R^6$ is equal to chlorine or bromine and x and y have the same or a different meaning.

The silicon-containing sulfides of the formula (1) are per se known compounds and may be produced by current processes, as described, for example, in the German AS 10 00 817. Examples for such compounds are (H₃CO)₃Si—CH₂—S—CH₂—Si(OCH₃)₃,
(H₅C₂O)₃Si—CH₂—S—CH₂—Si(OC₂H₅)₃,
(H₃CO)₃Si—CH₂CH₂—S—CH₂CH₂—Si(OCH₃)₃,
Cl₃Si—CH₂CH₂—Si—CH₂CH₂—SiCl₃,
(H₃CO)₃Si—CH₂CH₂CH₂—S—CH₂CH₂CH₂—Si(OCH₃)₃,
(H₃C)₂(H₃CO)Si—CH₂CH₂—S—CH₂CH₂—Si(OCH₃)(CH₃)₂,
(H₃CO)₃—Si—CH₂CH₂—S—CH₂CH₂—Si(OCH₃)₃,

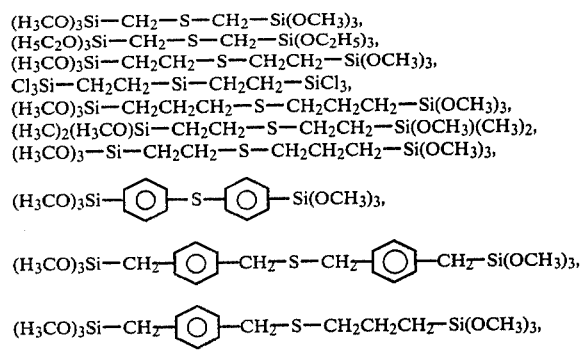

One advantage of the rhodium complexes of the invention with ligands of formula (1) as compared to the initially mentioned prior known sulfur containing rhodium compounds, resides especially in that they may easily be transformed into a form, which is insoluble in organic media and therefore in the situation regarding use as catalysts makes possible an easy separation of liquid components of the reaction mixture by filtration, centrifuging or decanting. As a result of this so-called "heterogenization", the rhodium losses may be reduced to a minimum. They permit a heterogenization by chemical fixation on the surface of certain carrier substances, whereby the two silicon atoms are bound via oxygen bridges to the carrier. But, they may also be converted to polymeric solid substances, whenever they are provided with tri-functional groups on the silicon.

The stoichiometric composition of the new rhodium compounds may be described by the formulae:
$RhX(CO)_2L$, $RhX(CO)L_2$, $[RhX(CO)L]_2$ $[RH(CO)L_2]_2$, $RhXL_3$, $RhX_3L_3$, $RhH(CO)L_3$, $RhH(CO)_2L_2$ as well as $RhHL_4$ in which the rhodium is present in the valency stages 0, +1 or +3, L represents a ligand of formula (1) and X stands for chloride, bromide, iodide, acetate, trifluoroacetate or trifluoropropionate.

The complex compounds of the stoichiometric compound $RhX_3L_3$ is particularly preferred, in which sulfide compounds of formula (1) are present as ligands, and X stands for chloride, bromide, iodide, acetate, trifluoroacetate or trifluoro-propionate. With a view to their use they may be activated as catalysts or may be influenced in their selectivity, whenever they are after-treated in a solvent, such as benzene, toluene, xylene, n-hexane, cyclohexane, methyl cyclohexane, monoglyme, di-ethylether tetrahydrofurane, dioxane and especially lower alcohols (e.g. 1 to 5 carbons) with H₂ and CO at total pressure of 10 to 300 bar and temperatures of 50 to 200° C.

Complex compounds of the stoichiometric composition of $RhCl(CO)L_2$ are also preferred, in which sulfide compounds of formula (1) are present as ligands L.

During their catalytic use, a change in the valency stage of the rhodium, as well as a change in regard to the number and type of the bound ligands may take place, just as X in the formula RhX₃L₃ may be replaced partially by hydrogen and the sulfide ligands L in the formulas RhX₃L₃ and RhCl(CO)L₂ may be partially replaced by other donors such as carbon monoxide, olefins, amines, phosphines or nitriles.

The production of the preferred rhodium complex RhX₃L₃ is accomplished, by reacting sulfides of the general formula (1) with anhydrous salts of a halogen acid or of a lower organic carboxylic acid containing possibly easily displaceable ligands, preferably low aliphatic nitriles or benzonitriles. Their catalytic activity may be influenced, in that they are after-treated in a solvent, such as benzene, toluene, xylene, n-hexane cyclohexane, methyl cyclohexane, monoglyme, diethyl ether, tetrahydrofurane, dioxane and particularly lower alcohols, with hydrogen and carbon monoxide at total pressure of about 10 to 300 bar and at temperatures of 50°-200° C.

The complexes RhX₃L₃ thus may be produced easily by reaction of the sulfides as in formula (1), with known easily accessible compounds, such as for example, RhCl₃.3H₂O, RhBr₃.2H₂O, RhI₃, RhCl₃(CH₃CN)₃, RhCl₃(C₂H₅CN)₃, RhCl₃(C₆H₅CN)₃, RhBr₃(CH₃CN)₃ or other rhodium systems, which carry easily substitutable ligands. In practice RhCl₃.3H₂O and RhCl₃(CH₃CN)₃, the preparation of which is described by B. F. G. Johnson and R. A. Walton in J. Inorg. Nucl. Chem. 28, 1901 (1966) are preferred.

For a pure production of complexes of the composition RhX₃L₃ according to the invention, it is necessarily required because of the hydrolysis-sensitive silicon-positioned groups, to use an anhydrous rhodium starting compound, such as for example, RhI₃ or RhCl₃ or RhCl₃(CH₃CN)₃, whereby then the reaction takes its course according to the following equation:

$$RhCl_3(CH_3CN)_3 + 3L \rightarrow RhCl_3L_3 + 3CH_3CN \quad (I)$$

The reaction may be carried out in the pure substance state, preferably however in non-polar or polar, inert as well as anhydrous solvents and takes its course even at room temperature; and for its acceleration it may be advantageous to use temperatures between 20° C. and the reflux temperature of the solvent used. In order not to make the purification of the compounds produced unnecessarily difficult, preferably almost stoichiometric quantities of sulfide-ligands L of formula (1) are used. By a halogen exchange on the central atom it will also be possible to synthesize the bromides and iodides RhBr₃L₃ and RhI₃L₃ according to the following equation II:

$$RhCl_3L_3 + 3NaBr \xrightarrow{Acetone} RhBr_3L_3 + 3NaCl \quad (II)$$

The complex compounds of the type of the formula RhCl(CO)L₂ may be produced by reacting sulfides of the general formula (1) with [Rh(CO)₂Cl]₂ at a temperature below 100° C., whereby the reaction is accomplished in a non-polar or polar, inert as well as anhydrous solvent, such as benzene, toluene, n-hexane, n-pentane cyclohexane, methyl-cyclohexane, petroleum ether, methanol, ethanol, propanol, iso-propanol, diethylether, tetrahydrofurane, monoethylene glycoldimethylether, or acetone at temperatures between room temperature and boiling temperature of the solvent.

Therefore, in this case one starts with $[Rh(CO)_2Cl]_2$, the preparation of which is given in Inorg. Synth. 8, 211 (1966) and one operates according to the following equation III, whereby in case of adhering to the required stoichiometry, the first formed intermediate stage of the composition $RhCl(CO)_2L$ may be isolated:

$$[Rh(CO)_2Cl]_2 + 4L \rightarrow 2RhCl(CO)L_2 + 2CO \quad (III)$$

The reaction according to equation III, may be accomplished both at room temperature as well as at higher temperatures. The latter will have a positive effect with a view to the reaction time, but, whenever the temperature is more than 100° C., it may also cause a decomposition of the product. The solvents used for this synthesis may have both a polar as well as a nonpolar character; to be sure, they must not enter into competitive or secondary reactions with the silicon-position groups, which is true generally for the equations I–III, and for the case under discussion of pure production of the complex compounds according to the invention, they must be substantially free from water.

As has already been mentioned, the advantage of the complex compounds of the invention, especially of those of the formula $RhX_3L_3$ resides in the fact that they are easily heterogenizable, i.e., they may be converted into a difficulty soluble form, which, while maintaining its characteristics permits its use according to current techniques in the heterogenous catalysis. This may be accomplished in such a way that the L groups $R^1$, $OR^2$ and $OR^5$, $R^6$ present on the ligand L, are partially or completely split off by hydrolysis in the form of alcohols or phenols, or else in the form of HCl or HBr and the remaining, alkylene sulfide- or arylene sulfide carrying silicon atoms build up a polymeric structure. At the same time it depends on the number of functional groups bound on the silicon, whether a syrupy mass develops, or a structure with silicic-acid-like character.

An essential object of the invention are polymeric compounds, barely or difficultly soluble in organic solvents, with a silicic-acid-like structure and the function of a rhodium carrier, to which rhodium salts of a halogen acid, possibly containing carbon monoxide, olefin, amine, phosphine or nitrile ligands, or crystal water or of a lower organic carboxylic acid are bound coordinatively by way of at least one ligand L', whereby L' signifies a sulfide compound L with trifunctionally substituted silicon of the formula (1), in which the originally present groups $OR^2$ and $OR^5$ as well as $R^1$ and $R^6$, the latter preferably as chlorine or bromine ions, are split off partially or completely hydrolytically as alcohol or phenol or HCl or HBr, and in which a rhodium sulfide ratio ranging from 1:1 to $1:10^6$, and which are preserved through the fact that complex compounds of the stoichiometric composition $RhX_3L_3$, in which L represents at least one ligand of the formula (1), and carbon monoxide, olefin, amine, phosphine or nitrile, or crystal water bound to possibly still free coordination places, and X is chlorine, bromine, iodine, acetate, trifluoroacetate or trifluoropropionate are reacted with water or an aqueous acid solution, possibly in the presence of an excess of the sulfide L beyond the stoichiometric composition $RhX_3L_3$ and/or in the presence of cross-linking agents, such as methyl or ethyl silicate, eventually while distilling off the alcohol or phenol that is formed, or else in that the ligand L, possibly in the presence of cross-linking agents of the cited type is reacted with water or an aqueous acid solution, eventually while distilling off the alcohol or phenol that is formed and in that the solid substance formed is reacted with rhodium compounds representing hydrous or anhydrous salts of a halogen acid or of a lower carboxylic acid, and carrying possibly easily displaceable ligands, preferably low aliphatic nitriles or benzonitrile, or of the compound $[Rh(CO)_2Cl]_2$.

The process for the production of the previously characterized polymers is also an object of the invention. In detail, it is characterized, in that complex compounds of the stoichiometric composition $RhX_3L_3$, in which L represents at least a ligand of the formula (1), provided with trifunctionally substituted silicon and carbon monoxide, olefin, amine, phosphine or nitrile, or crystal water bound to possibly still free places of coordination, and X is as defined above, are reacted with water or an aqueous acid solution, possibly in the presence of an excess of the sulfide L beyond the stoichiometric composition $RhX_3L_3$ and/or in the presence of cross-linking agents, such as methyl or ethylsilicate, eventually with simultaneous or succeeding distillation removal of the alcohol or phenol that is formed, or else in that one reacts the ligand L, possibly in the presence of cross-linking agents of the type mentioned, with water or an aqueous acid solution, possibly with simultaneous or succeeding distillative removal of the alcohol or phenol that is formed, and in that the formed solid substance is reacted with rhodium compounds, representing hydrous or anhydrous salts of a halogen acid or of a lower carboxylic acid and carrying possibly easily displaceable ligands, preferably lower aliphatic nitriles or benzonitriles, or else with the compound $[Rh(CO)_2Cl]_2$.

For the conversion of a complex of the type $RhX_3L_3$ with ligands L of the formula (1)—$RhCl_3L_3$ with trifunctional substituted silicon is preferred—into its difficulty soluble form one will therefore proceed best in such a way that the rhodium complex, present in pure substance or else dissolved in an organic solvent, is treated at room temperature or at increased temperature with an excess quantity of water and, in order to achieve as quantitative a hydrolysis as possible, the alcohol or the phenol that is formed is removed by simultaneously or subsequently distilling from the reaction mixture. The heterogenization will be particularly simple in case of ligands, which have chlorine or bromine atoms, silicon positioned and which build up a silicic acid like structure upon HCl or HBr separation. This method will permit in particular to insert also more ligand L into the precipitated product, than are required according to the stoichiometry of the formula $RhX_3L_3$, whereby, effectively, a mixture, consisting of the desired quantity of ligands L, the $RhX_3L_3$-complex and perhaps a solvent, is hydrolyzed. In this way, the shelf life, the selectivity and the activity of the catalyst may be influenced, beyond that, the detachment of the rhodium from the ligand-containing solid substance is made considerably more difficult. By the presence of so-called cross linking agents, which likewise represent easily hydrolizable compounds, such as for example, $Si(OC_2H_5)_4$, the precipitation may also be facilitated and the density of the sulfide groups in the precipitated product may be varied. For the incorporation of large excesses of free ligand L into the precipitated product one best uses for the hydrolysis a diluted aqueous acid solution, preferably diluted hydrochloric acid into which the dissolved or undissolved mixture of the pertinent ligand L and the $RhX_3L_3$-complex, preferably $RhCl_3L_3$, is added dropwise whereby one may just as well proceed in reverse.

In practice, one does not start out from the pure $RhX_3L_3$ compounds for the production of such a "heterogenized" catalyst, in case of which the polymeric ligands simultaneously have the function of a carrier and which may have an atomic Rh:S ratio of 1:1 to $1:10^6$, but one reacts a rhodium compound from the series $RhCl_3.3H_2O$, $RhBr_3.2H_2O$, $RhI_3$, $RhCl_3(CH_3CN)_3$, $RhCl_3(C_2H_5CN)_3$, $RhCl_3(C_6H_5CN)_3$, $RhBr_3(CH_3CN)_3$ or other rhodium systems, which carry easily substituted ligands, with the desired quantity of sulfide compound L of formula (1) in pure substance or in solution to the complex compound $RhX_3L_3$ and hydrolyzes the latter possibly after a change of the solvent in order to avoid a back reaction, thus for example, after replacement of ethanol by toluene, with water or an aqueous acid solution, may be while distilling off the alcohol or phenol that is formed, under precipitation.

The use of a carrier, to which the rhodium complexes may be bound by way of the silicon groupings to the sulfide ligand, represents another alternative thereto. Suitable carrier materials are above all inorganic substances which have reactive surface groups, especially acid OH groups, which may react under alcohol or phenol or HCl or HBr separation with the $SiOR^2$-, $SiOR^5$- or $SiR^1$-, $SiR^6$ units according to formula 1 while building up the carrier-O-Si-bonds, and which by the double linkage places per ligand insure a particularly strong linkage between the rhodium complex and the carrier material.

Another object of the invention therefore, relates to rhodium complex compounds bound by way of inorganic carriers, having surface positioned oxygen atoms, of the type

$RhX_3L_3$ and $RhCl(CO)L_2$, whereby X is defined as above, and L represents at least a ligand of the formula (1) and carbon monoxide, olefin, amine, phosphine or nitrile, or crystal water possibly bound to still free places of coordination, by way of reaction of the acid hydrogen with originally present groups $OR^2$ and $OR^5$ or $R^1$ and $R^6$, the latter preferably as chlorine or bromine ions, with alcohol or phenol or else under HCl or HBr separation the bond to the carrier is established, whereby on the carrier possibly uncoordinated radicals of the sulfide L are still bound and the rhodium: sulfide ratios range from 1:1 to $1:10^3$, and which are obtained by providing a solution of the compound $RhX_3L_3$ or $RhCl(CO)L_2$—, possibly in the presence of excess sulfides L of the formula 1, and treating within the scope of the provided quantitative parameters, with a suspension of the carrier material in an inert organic solvent at temperatures between room temperature and the reflux temperature of the suspension agent used, or else a sulfide of the formula 1 is treated with a suspension of the carrier material in an inert organic solvent at the temperature conditions mentioned, and further that subsequently the solid substance formed is reacted with rhodium compounds representing anhydrous or hydrous salts of a halogen acid or of a lower carboxylic acid and carrying possibly easily displaceable ligands, preferably lower aliphatic nitriles or benzonitrile or with the compound $[Rh(CO)_2Cl]_2$.

Although the selection of the carrier substances to be used is not limited, nevertheless the following carrier substances proved to be particularly suitable: pyrogeneous or precipitated silicic acid, quartz, a silicate glass, silicagel, titanium dioxide, zirconium dioxide, a zeolite, aluminum oxide, Kaolin, bauxite, diatomaceous earth, or another substance, built up from aluminum and silicon and salts or oxides of additional metals with acid OH groups.

For the production of carrier-fixed rhodium complex compounds, in detail a method of processing has proven advantageous, wherein a solution of the compound $RhX_3L_3$ or $RhCl(CO)L_2$, possibly in the presence of excess sulfides L of the formula (1), is treated with a suspension of the carrier material in an inert organic solvent at temperatures between room temperature and the reflux temperature of the suspension agent used, or else a sulfide of the formula (1) is treated with a suspension of the carrier material in an inert organic solvent at the stated temperature conditions; and subsequently the formed solid substance is reacted with rhodium compounds, such as anhydrous or hydrous salts of a halogen acid or of a lower carboxylic acid and carrying possibly easily displaceable ligands, preferably lower aliphatic nitriles or benzonitrile, or with the compound $[Rh(CO)_2Cl]_2$.

According to an embodiment, effective in practice, of the process of the invention, one proceeds in such a way, that one reacts a rhodium compound from the series $RhCl_3.3H_2O$, $RhBr_3.2H_2O$, $RhI_3$, $RhCl_3(CH_3CN)_3$, $RhCl_3(C_2H_5CN)_3$, $RhCl_3(C_6H_5CN)_3$, $RhBr_3(CH_3CN)_3$ and $[Rh(CO)_2Cl]_2$ or from other rhodium systems which carry easily substitutable ligands with the desired quantity of sulfide compound L of formula (1) in pure substance, or in solution into the complex compound $RhX_3L_3$ or $RhCl(CO)L_2$, and in that the latter are treated, possibly after a change of the solvent in order to avoid a back reaction, thus for example, replacement of ethanol by toluene, with a suspension of the carrier material.

In order to avoid a hydrolysis of the moisture-sensitive functional groups on silicon, naturally a starting complex as free of water as possible is chosen, such as for example, $RhCl_3(CH_3CN)_3$ and is reacted with the calculated volume of the sulfide bond, whereby the atomic ratio between rhodium and sulfur may range from 1:1 to $1:10^3$. Thereupon takes place effectively at elevated temperature the direct further reaction with a suspension of the carrier material. A reverse method of proceeding—primary fixation of the ligand L on the carrier and subsequent reaction with, for example, $RhCl_3(CH_3CN)_3$—is likewise possible. Suitable solvents for the production of the sulfide groups carrying complex as well as for its fixation, are, for example, benzene, toluene, xylene, cyclohexane or n-hexane. In case of the production and in case of the fixation of the rhodium complex, one preferably applies higher temperatures although both stages may also be carried out at room temperature.

The rhodium-containing substances produced with or without use of a carrier, that means the polymerized and the carrier-fixated complex compounds, may be optimized with a view to their use as catalysts in regard to activity and selectivity. In addition the polymeric solid substance or the carrier-fixed rhodium complex compounds may be after-treated in one stage or multi-stage at total pressures of about 10 to 300 bar and temperatures of 50° to 200° C. with hydrogen-carbon monoxide mixtures and/or with reduction agents, such as formaldehyde, alkali or earth alkaline borohydride, borane compounds, lithium aluminum hydride, or hydrazine, preferably in the presence of a solvent, such as benzene, toluene, xylene, n-hexane, cyclohexane, methylcyclohexane, monoglyme, diethyl ether, tetrahydrofurane, dioxane and especially lower alcohols. A reduction treatment is also possible under certain circumstances.

The soluble, precipitated rhodium complexes of the invention, bound to the carrier, but above all their reduced forms, represent outstanding catalysts for hydroformylation, hydrogenation, carboxy methylation and isomerization reactions as well as for reactions of CO with $H_2$. The soluble catalysts, may also be separated in this form from the reaction mixture and heterogenized by polymerization or carrier fixation, after they had been used in homogenous systems for catalytic processes. Whenever the heterogenization is not to take its course toward the solid substance but to a syrupy mass, then one starts with monomeric complex compounds, in which the silicon has been difunctionally substituted. In case of heterogenization by carrier fixation the functionality of the silicon-positioned groups plays a subordinate role.

Finally, another object of the invention resides in the use of the monomeric, polymeric and carrier-fixed rhodium complex compounds as catalysts for chemical reactions.

Thus, the hydroformulation of olefins, employing the new catalysts may be carried out in a manner known per se at hydrogen/carbon monoxide overall pressures of 10–1000 bar and temperatures of about 70°–200° C., with or without the use of a solvent, whereby the high selectivity of the catalysts of the invention permits the subsequent production of aldehydes or that of the corresponding alcohols.

The hydrogenation of olefinic groupings may be carried out at room temperature or at higher temperatures, at under or above atmospheric pressure, and naturally at atmospheric pressure. At the same time, the "heterogenized" rhodium sulfide complexes show partially comparable activities such as homogeneous systems, for example, such as the homogeneously used rhodium-phosphin complex RhCl $[P(C_6H_5)_3]_3$, but as compared to the latter, they have above all the advantages of a far longer catalyst shelf life and an easier separability of other components of the reaction mixture such as solvents, substrate or product.

The "heterogenized" catalysts of the invention may be isolated from the reaction medium by decanting, centrifuging, or filtering and may again be inserted, without any loss in activity being determinable, and without even the slightest part of rhodium containing compound being determinable.

The "heterogenizable" monomeric catalysts of the invention, on the basis of the presence of two silicon atoms per ligand L, with suitable functionalization, permit both intra as well as inter molecular condensation reactions, as a result of which in cooperation with the selected condensation conditions, the particle structure of a polymer, to be produced by heterogenization, may be influenced.

In case of heterogenization, the kind of functionalizing at both silicon atoms will permit an influence on the physical behavior of the solid substances as compared to solvents or components of reaction mixtures by carrier fixation, by means of which, for example, a desired suspendibility or wettability may be adjusted in such media.

The invention will be further explained subsequently on the basis of embodiments by way of example. The special sulfide ligands L of the formula (1), used according to the invention in the case of these examples in the systems $RhX_3L_3$ and $RhCl(CO)L_2$, represent simple and easily accessible representatives of their kind and consequently have the character of models. Particularly the generally known characteristics of silicon-organic compounds of this type justify this statement and also the fact that the sulfide ligands of the new rhodium complexes, as compared to the status of the prior art. (German OS No. 24 53 229, Germ. OS No. 24 05 274, Germ. OS No. 25 50 660) are not essentially changed in their ligand qualities, i.e., in their capacity for coordination. Therefore, an analogous conclusion for other species of L, usable within the scope of the invention, because it is self-evident for every expert, is justified. Corresponding conclusions are also valid naturally for the anion X used.

EXAMPLE 1

0.935 g (2.81 m moles) $RhCl_3(CH_3CN)_3$ and 3.85 g (9.28 m moles) $S[(CH_2)_2Si(OC_2H_5)_3]_2$ were united in 60 ml of dry toluene, and the solution was heated for 16 hours in an atmosphere of purified and dried nitrogen under reflux. Subsequently, the solution was filtered off and the solvent was distilled away in the vacuum. The remaining oil was absorbed in 40 ml warm, dry n-pentane and was crystallized out at temperatures of $< -80°$ C. This process was repeated once more. After drying at 50° C./$10^{-2}$ mbar, 3.95 g. $RhCl_3\{S[(CH_2)_2Si(OC_2H_5)_3]_2\}_3$ were obtained in the form of an orange-red, viscous oil (96.6% of theory related to $RhCl_3(CH_3CN)_3$).

| Analyses: | C%    | H%   | Cl%  | S%   | Rh%  |
|-----------|-------|------|------|------|------|
| Theory:   | 39.67 | 7.91 | 7.32 | 6.62 | 7.08 |
| Found:    | 39.33 | 7.55 | 7.52 | 6.18 | 6.88 |

The composition was confirmed by IR and NMR spectroscopy.

EXAMPLE 2

0.875 g (2.63 m mole) $RhCl_3(CH_3CN)_3$ and 3.11 g (8.67 m mole) $S[(CH_2)_3Si(OCH_3)_3]_2$ were united in 60 ml dry toluene and the solution was stirred for 20 hours in a nitrogen atmosphere at the reflux temperature. After that it was filtered off from insoluble components of the mixture and the solvent was removed under vacuum. The oily residue was absorbed in warm dry n-hexane and was crystallized out in a dry-ice/methanol bath. The purification step was repeated and the orange-red, viscous oil obtained was dried at 50° C./$10^{-2}$ m bar 3.32 g of $RhCl_3 \{S[(CH_2)_3Si(OCH_3)_3]_2\}_3$ were isolated (98.2% of theory related to $RhCl_3(CH_3CN)_3$.

| Analyses: | C%    | H%   | Cl%  | S%   | Rh%  |
|-----------|-------|------|------|------|------|
| Theory:   | 33.65 | 7.06 | 8.28 | 7.48 | 8.01 |
| Found:    | 33.45 | 6.87 | 8.82 | 7.08 | 7.53 |

The composition was confirmed by IR and NMR spectroscopy.

EXAMPLE 3

From 0.804 g (2.42 m Mole) $RhCl_3(CH_3CN)_3$ and 4.53 g (7.99 m Mole)

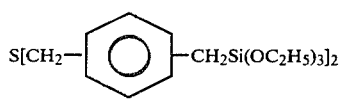

there were obtained analogously to example 2, 4.437 g of $RhCl_3$

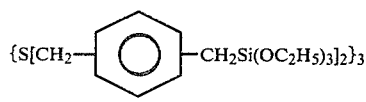

(96.0% of theory related to $RhCl_3(CH_3CN)_3$).

| Analyses: | C% | H% | Cl% | S% | Rh% |
|---|---|---|---|---|---|
| Theory | 17.61 | 2.43 | 5.57 | 5.04 | 5.39 |
| Found: | 17.46 | 2.60 | 5.38 | 5.06 | 5.22 |

The substance was further characterized by IR and NMR spectroscopy; both spectra are characterized by the bonds of the sulfide ligands.

EXAMPLE 4

9.54 g (23.0 m Mole) $S[(CH_2)_2Si(OC_2H_5)_3]_2$, dissolved in 20 ml of dry n-hexane were added dropwise within 20 minutes into the boiling solution of 2.13 g (5.48 m Mole) $[Rh(CO)_2Cl]_2$ in 80 ml of dry n-hexane, and this mixture was heated another 3 days in a nitrogen atmosphere under reflux and IR spectroscopic control of the reaction on the basis of characteristic $\gamma CO$-oscillations. It was filtered off and the product was crystallized out at temperatures of $< -78°$ C. After renewed freezing out of 50 ml of n-pentane and subsequent drying at 50° C./$10^{-2}$ mbar, 10.4 g (95.3% of theory) $RhCl(CO)\{S[(CH_2)_2Si(OC_2H_5)_3]_2\}_2$ were obtained in the form of an oil colored yellowish-green in dilution.

| Analyses: | C% | H% | Cl% | S% | Rh% |
|---|---|---|---|---|---|
| Theory: | 39.80 | 7.69 | 3.56 | 6.44 | 10.33 |
| Found: | 38.50 | 6.97 | 3.36 | 6.45 | 9.94 |

The substance was further characterized by IR and HMR spectroscopy.

| IR-spectrum: | | $\gamma CO$ | |
|---|---|---|---|
| Molded piece | KBr | 1967 cm$^{-1}$ | (very strong) |
| solution | n-hexane | 1973, 1983 cm$^{-1}$ | (very strong) |

EXAMPLE 5

8.20 g (22.87 m Mole) $S[(CH_2)_3Si(OCH_3)_3]_2$, dissolved in 20 ml n-hexane were added dropwise within 15 minutes into the boiling solution of 2.10 g (5.40 m Mole) $[Rh(CO)_2Cl]_2$ in 80 of n-hexane and the mixture was heated another 3 days in a nitrogen atmosphere under reflux. It was filtered off and the product was made to crystallize at $-78°$($CO_2$/methanol). After re-absorption of the oil obtained in 50 ml of n-hexane, the renewed freezing out and drying at 50° C./$10^{-2}$ mbar, 9.40 g (98.5% of theory) of $RhCl(CO)\{S[(CH_2)_3Si(OCH_3)_3]_2\}_2$, in the form of a greenish yellow oil in dilution was obtained.

| Analyses: | C% | H% | Cl% | S% | Rh% |
|---|---|---|---|---|---|
| Theory: | 33.98 | 6.84 | 4.01 | 7.26 | 11.65 |
| Found: | 33.91 | 6.54 | 4.31 | 7.27 | 12.73 |

The substance was furthermore characterized by IR and NMR spectroscopy.

| IR spectrum | | $\gamma CO$ | |
|---|---|---|---|
| Molded piece | KBr | 1965 cm$^{-1}$ | (very strong) |
| solution | n-hexane | 1970, 1980 cm$^{-1}$ | (very strong) |

EXAMPLES 6–12

General operating instructions for the "heterogenisation" of various compounds of the type $RhCl_3L_3$ by means of polymerization.

$RhCl_3.3H_2O$ was first dissolved in warm ethanol. The calculated quantity of silicon-containing sulfide compound was added to this solution and the mixture was stirred for about 2–3 hours under reflux. Subsequently, the solvent was distilled off, whereby a dark red, oily residue remained in the flask. This was absorbed in hot toluene and was stirred until a clear solution was obtained. An excess quantity of water was then dropped in slowly in the heat.

Even after the first drops, a voluminous, more or less intensively orange colored solid substance resulted. Stirring under reflux was continued for yet at least 2 hours, and then at first one toluene/ethanol/$H_2O$-azeotrope and after that a toluene/$H_2O$-azeotrope was separated in the water separator. After the addition of more toluene it was filtered off hot, the remaining solid substance was extracted with hot toluene as well as ethanol altogether for 2 hours in the Soxhlet and dried at 100° C./$10^2$ mbar. The filtrates and/or extracts were as a rule almost colorless, which gave rise to the conclusion of an approximately quantitative precipitation of the rhodium-sulfide complexes.

In the case of example 10, tetraethyl silicate was used as a cross-linking agent. This was added to the reaction solution only briefly before the hydrolysis.

| | Starting Substances | | Quantities of | | | Yield related | |
|---|---|---|---|---|---|---|---|
| | Rhodium | | Solvent | | $H_2O$ | to total | |
| Example | Component | Sulfide Component | Ethanol | Toluene | Quantity | weighed sample | |
| Nr. | (g) (mMole) | (g) | (ml) | (ml) | (ml) | (g) | (%)* |
| 6 | $RhCl_3 . 3H_2O$ | $S[(CH_2)_2Si(OC_2H_5)_3]_2$ | | | | | |
| | 1.08   4.11 | 5.96     14.36 | 50 | 50 + 50 | 5 | 3.53 | 97.4 |
| 7 | $RhCl_3 . 3H_2O$ | $S[(CH_2)_2Si(OC_2H_5)_3]_2$ | | | | | |
| | 0.57   2.17 | 5.39     13.00 | 50 | 50 + 50 | 5 | 2.90 | 98.2 |
| 8 | $RhCl_3 . 3H_2O$ | $S[(CH_2)_3Si(OCH_3)_3]_2$ | | | | | |

-continued

| Example Nr. | Starting Substances | | | | Quantities of | | H₂O Quantity (ml) | Yield related to total weighed sample | |
|---|---|---|---|---|---|---|---|---|---|
| | Rhodium Component | | Sulfide Component | | Solvent | | | | |
| | (g) | (mMole) | | (g) | Ethanol (ml) | Toluene (ml) | | (g) | (%)* |
| 9 | 0.895 RhCl₃ . 3H₂O | 3.40 | S[(CH₂)₃Si(OCH₃)₃]₂ | 4.26  11.88 | 50 | 50 + 50 | 4 | 3.328 | 100 |
| 10 | 1.53 RhCl₃ . 3H₂O | 5.80 | S[(CH₂)₃Si(OCH₃)₃]₂ | 12.50  34.86 | 50 | 50 + 20 | 8 | 8.85 | 99.5 |
| 11 | 1.46 RhCl₃ . 3H₂O | 5.54 | S[(CH₂)₃Si(OCH₃)₃]₂<br>Si(OC₂H₅)₄ | 7.00  19.52<br>8.13  39.02 | 50 | 50 + 50 | 8 | 8.34 | 106.8 |
| 12 | 1.43 RhCl₃ . 3H₂O | 5.43 | S[(CH₂)₅Si(OCH₃)₃]₂ | 7.89  19.02 | 60 | 50 + 50 | 5 | 6.38 | 99.7 |
| | 1.40 | 5.32 | S[(CH₂—⟨C₆H₄⟩—CH₂—Si(OC₂H₅)₃]₂ | 9.95  17.55 | 60 | 50 + 50 | 5 | 7.05 | 98.5 |

*Related to the quantity of precipitated products, to be expected in case of complete hydrolysis.

| Example Nr. | | Product Analyses | | | | |
|---|---|---|---|---|---|---|
| | | Rh (%) | Ch (%) | S (%) | C (%) | H (%) |
| 6 | Theory | 11.66 | 12.05 | 12.72 | 19.06 | 3.20 |
| | Found | 12.18 | 10.96 | 11.43 | 19.35 | 3.65 |
| 7 | Theory | 7.55 | 7.80 | 14.11 | 21.14 | 3.55 |
| | Found | 7.60 | 8.13 | 13.20 | 20.68 | 3.74 |
| 8 | Theory | 10.50 | 10.85 | 11.44 | 25.72 | 4.32 |
| | Found | 9.35 | 10.96 | 11.01 | 25.30 | 4.56 |
| 9 | Theory | 6.71 | 6.93 | 12.56 | 28.24 | 4.74 |
| | Found | 5.75 | 7.05 | 12.17 | 29.05 | 4.87 |
| 10 | Theory | 7.30 | 7.55 | 8.02 | 18.02 | 3.02 |
| | Found | 6.80 | 7.03 | 7.79 | 18.08 | 3.86 |
| 11 | Theory | 8.74 | 9.03 | 9.53 | 35.72 | 6.00 |
| | Found | 8.02 | 8.74 | 9.01 | 35.90 | 6.44 |
| 12 | Theory | 7.65 | 7.90 | 7.86 | 47.11 | 3.95 |
| | Found | 7.44 | 8.11 | 7.71 | 47.85 | 4.36 |

EXAMPLE 13

1.5 g (4.51 m Mole) RhCl₃(CH₃CN)₃ and 8.03 g (22.50 m Mole) S[CH₂CH₂SiCl₃]₂ were united in 60 ml of dry toluene and the solution was stirred for 10 hours under reflux. Subsequently traces of difficulty soluble components of the reaction mixture were filtered off and the filtrate was reacted with 8 ml H₂O drop by drop. After another 2 hours of reflux boiling of the developed suspension, aqueous HCl solution liberated acetonitrile and a part of the toluene were distilled off, 50 ml of fresh toluene was added and the orange colored solid substance was filtered off, and was extracted for 8 hours as well on the Soxhlet. After 3 hours of drying at 110° C./10⁻² mbar, 5.1 g (96.7% of theory) of the product was obtained.

In case of complete hydrolysis and precipitation the following analytical values were to be expected:

| C% | H% | Rh% | Cl% | S% |
|---|---|---|---|---|
| 20.51 | 3.44 | 8.80 | 9.10 | 13.68 |

The following were found:

| C% | H% | Rh% | Cl% | S% |
|---|---|---|---|---|
| 20.10 | 3.09 | 8.39 | 10.22 | 13.20 |

EXAMPLE 14

The clear solution of 0.256 g (0.973 m Mole) RhCl₃.3H₂O in 80 ml of dried ethanol was reacted with 34.89 g (97.3 m Mole) S[(CH₂)₃Si(OCH₃)₃]₂ and was heated to boiling for 2 hours. The solvent was distilled off and the oily residue was absorbed in 50 ml of dry toluene. This solution was transferred to a dropping funnel and was added dropwise within about 1 hour into 40 ml hot, 2 N—HCl solution. The deposit thus formed was stirred vigorously for yet another 4 hours at 100° C. Subsequently, the alcohol formed and the aqueous HCl solution were removed from the reaction mixture by distillation. After addition of another 50 ml of toluene, the solid substance was filtered off, was extracted with toluene as well as with ethanol in the Soxhlet (altogether 24 hours) and was dried for 3 hours at 110° C./10⁻² mbar. 19.49 g (90% of theory) of a yellow powder were obtained.

In case of complex alcohol elimination and quantitative precipitation the following analytical values were to be expected:

| | C% | H% | Rh% | Cl% | S% |
|---|---|---|---|---|---|
| The following were found: | 32.39 | 5.44 | 0.463 | 0.478 | 14.41 |
| | 30.03 | 5.56 | 0.49 | 0.87 | 12.8 |

EXAMPLES 15-23

General operating instructions for fixation of different compounds of the type RhCl₃L₃ (L=sulfide ligand of formula 1) to organic carriers, which have acid OH-groups:

The calculated quantities of RhCl₃(CH₃CN)₃ and sulfide component were always united in 50 ml of dry toluene and the solution was stirred under reflux between 3 and 12 hours, depending on the portion of sulfide. Subsequently, this was transferred to a dropping funnel, and, within 15 minutes, it was added dropwise into the vigorously stirred suspension of 20 g of dried carrier material in 250 ml toluene. After another 48 hours of stirring under reflux, the solvent was removed by distillation, the product which remained in the flask and was lightly orange colored, was transferred into an extraction thimble, was extracted with toluene for 24 hours and was then dried at 110° C./10⁻² mbar.

General operating instructions for the fixation of various compounds of the type RhCl (CO)L$_2$(L=sulfide ligand of formula 1) to inorganic carriers which have acid OH-groups:

The calculated quantities [Rh(CO)$_2$Cl]$_2$ and the sulfide component were united in 40 ml of dry n-hexane, and the solution was stirred under reflux for 2-3 days, depending on the portion of sulfide. Subsequently, one proceeded analogously to the preceeding instructions, however, instead of toluene, n-hexane was used. The reaction time with the carrier material was extended to 60 hours.

yellowish green color as a result of this treatment. Weighed product: 2.9 g.

In the IR-spectroscopic examination of the product (as KI molded piece) a new band was observable at 1967 cm$^{-1}$, in case of which we are dealing in all probability with a $\gamma$CO oscillation.

EXAMPLE 25

0.988 g of a substance, containing rhodium-sulfide complex, produced analogously to example 14, with a rhodium content of 5.3%, a chlorine content of 8.03% and an S content of 9.77% were suspended in 40 ml of

| | Starting Substances | | | | | |
|---|---|---|---|---|---|---|
| | Rhodium Compound | | Sulfide Component | | Reaction Time | |
| Example Nr. | (mg) | (mMole) | (mg) | (mMole) | (h) | Carrier Material |
| 15 | RhCl$_3$(CH$_3$CN)$_3$ 166.21 | 0.5 | S[(CH$_2$)$_2$Si(OC$_2$H$_5$)$_3$]$_2$ 622.06 | 1.5 | 12 | Aerosil 200 0.6 mMol SiOH/g |
| 16 | RhCl$_3$(CH$_3$CN)$_3$ 166.21 | 0.5 | S[(CH$_2$)$_2$Si(OC$_2$H$_5$)$_3$]$_2$ 1451.5 | 3.5 | 3 | Aerosil 200 0.6 mMol SiOH/g |
| 17 | RhCl$_3$(CH$_3$CN)$_3$ 166.21 | 0.5 | S[(CH$_2$)$_3$Si(OCH$_3$)$_3$]$_2$ 537.9 | 1.5 | 12 | Aerosil 200 0.6 mMol SiOH/g |
| 18 | RhCl$_3$(CH$_3$CN)$_3$ 166.21 | 0.5 | S[(CH$_2$)$_3$Si(OCH$_3$)$_3$]$_2$ 896.5 | 2,5 | 8 | Aerosil 200 0.6 mMol SiOH/g |
| 19 | RhCl$_3$(CH$_3$CN)$_3$ 166.21 | 0.5 | S[(CH$_2$)$_3$Si(OCH$_3$)$_3$]$_2$ 896.5 | 2.5 | 8 | Ultrasil VN 3 1.2 mMol SiOH/g |
| 20 | RhCl$_3$(CH$_3$CN)$_3$ 166.21 | 0.5 | S[(CH$_2$)$_3$Si(OCH$_3$)$_3$]$_2$ 2689.5 | 7.5 | 3 | Ultrasil VN 3 1.2 mMol SiOH/g |
| 21 | RhCl$_3$(CH$_3$CN)$_3$ 332.42 | 1.0 | S[(CH$_2$)$_3$Si(C$_6$H$_5$)$_2$OC$_2$H$_5$]$_2$ 1712.82 | 3.0 | 12 | Ultrasil VN 3 1.2 mMol SiOH/g |
| 22 | RhCl$_3$(CH$_3$CN)$_3$ 166.21 | 0.5 | S[(CH$_2$)$_3$Si(OCH$_3$)$_3$]$_2$ 896.5 | 2.5 | 9 | Titanium dioxide P25 |
| 23 | [Rh(CO)$_2$Cl]$_2$ 97.19 | 0.25 | S[(CH$_2$)$_2$Si(OC$_2$H$_5$)$_3$]$_2$ 414.7 | 1.0 | 72 | Aerosil 200 0.6 mMol SiOH/g |

| | Product Analyses | | | |
|---|---|---|---|---|
| Example Nr. | | Rh (%) | Cl (%) | S (%) |
| 15 | Theory | 0.254 | 0.263 | 0.237 |
| | Found | 0.20 | 0.30 | 0.23 |
| 16 | Theory | 0.25 | 0.258 | 0.544 |
| | Found | 0.26 | 0.34 | 0.49 |
| 17 | Theory | 0.252 | 0.26 | 0.235 |
| | Found | 0.23 | 0.33 | 0.23 |
| 18 | Theory | 0.25 | 0.26 | 0.39 |
| | Found | 0.18 | 0.30 | 0.40 |
| 19 | Theory | 0.25 | 0.26 | 0.39 |
| | Found | 0.23 | 0.33 | 0.47 |
| 20 | Theory | 0.24 | 0.25 | 1.12 |
| | Found | 0.24 | 0.35 | 1.09 |
| 21 | Theory | 0.475 | 0.49 | 0.44 |
| | Found | 0.46 | 0.48 | 0.52 |
| 22 | Theory | 0.25 | 0.26 | 0.39 |
| | Found | 0.24 | 0.30 | 0.36 |
| 23 | Theory | 0.25 | 0.09 | 0.16 |
| | Found | 0.28 | 0.12 | 0.17 |

EXAMPLE 24

7 ml of 35% aqueous CH$_2$O-solution, diluted with 10 ml of ethanol were dropped within 15 minutes into the suspension of 3 g of the "heterogenized" rhodium sulfide complex—produced as in example 9—in boiling ethanol, and the mixture was stirred under reflux for another hour. Subsequently, the solution of 0.7 NaBH$_4$ in 30 ml of ethanol was added in doses to that within about 10 minutes and again stirred under reflux for one more hour. The solid substance was then filtered off, was extracted on the Soxhlet with ethanol for 2 hours and finally dried for 3 hours at 100° C./10$^{-2}$ mbar. The previously orange colored substance had assumed a boiling-ethanol, and, while stirring vigorously, were reacted within 20 minutes with a solution of 313 mg of NaBH$_4$ in 25 ml of ethanol. This was stirred for another 2 hours under reflux and the solid substance, which in the meantime was no longer orange, but colored yellowish green, was filtered off, was extracted for 4 hours with ethanol in the Soxhlet and was dried for 2¼ hours at 110° C./10$^{-2}$ mbar.

EXAMPLE 26

The suspension of 10 g of the carrier-fixed rhodium complex, produced as in example 19, was reacted in 150 ml of ethanol in boiling heat within 15 minutes with 0.48 ml of 35% aqueous formaldehyde solution which was diluted additionally with 10 ml of ethanol, and the mixture was stirred under reflux for an additional hour. Following this, the solution of 45.5 mg NaBH$_4$ in 30 ml of ethanol was dropped into it within ten minutes, and heated once more under reflux for 2 hours. After filtering off of the solid substance, 4 hours of extracting with ethanol and drying at 100° C./10$^{-2}$ mbar, a part of the 9.5 g of catalyst obtained was used for hydrogenation of crotonic acid (example 33).

EXAMPLE 27

A mixture of 422 mg of the rhodium-sulfur compound (12.18 % Rh), obtained as in example 6, 62.5 ml of hexene-1 and 180 ml of toluene were exposed in a 500 ml lift autoclave to a CO/H$_2$ cold pressure (1:1) of 200 bar. Within 10 minutes, about 97% of the hexene-1 were converted at a temperature of 135° C., to n-heptanal and 2 methylhexanal. The composition of the reaction mixture was determined gas-chromatographically at about 47% n-heptanal, about 50% 2 methyl hexanal and about 3% hexene-1/n-hexane.

For the re-use, the undissolved catalyst was filtered off the liquid phase and washed out with toluene.

EXAMPLE 28

62.5 ml of hexene-1, dissolved in 180 ml of toluene were hydroformylated, using the separated catalyst of example 27 in a 500 ml lift autoclave at a $CO/H_2$ cold pressure (1:1) of 200 bar and at a temperature of 120° C. within 14 minutes. The loss of pressure developed thereby was again compensated for by adding pressure of CO and $H_2$ and 62.5 ml of hexene-1 was pumped again by means of a metering pump into the autoclave. The temperature was held at 120° C. The $H_2/CO$ absorption took place within 22 minutes. After a renewed complementation of the loss of pressure and of dosing 62.5 ml of hexene-1, no absorption of gas could be found even after 10 minutes. The autoclave was cooled and expanded. The gas-chromatographic examination of the reaction mixture showed that hydroformylation of hexene-1 had taken place at 98%, whereby about 53% n-heptanal and about 47% 2-methyl hexanal had been formed. The presence of not even the slightest quantities of the corresponding alcohols was observed.

EXAMPLE 29

62.5 ml of hexene-1 were converted within 40 minutes at more than 97%, with 677 mg of the catalyst model (7.60% Rh) obtained according to example 7, at a temperature of 115° C. and at an $H_2/CO$ total cold pressure (1:1) of 200 bar, into n-heptanal and 2 methyl hexanal. About 53% of straight chain and about 44% of branched aldehyde as well as about 3% of hexene-1/hexane were found as components of the reaction mixture by gas-chromatography.

EXAMPLE 30

After the reaction has taken place as in example 29, the catalyst used was filtered off, washed with toluene and again used for the hydroformylation of first 62.5 ml of hexene-1. This was carried out after adding pressure of 100 bar CO and $H_2$ in a total pressure area of 230-190 bar, but at a temperature of 180° C. After two additions each of 62.5 ml hexene-1 were after dosed in, whereby the total starting pressure was always adjusted again to 230 bar, the hexene-1 used according to a gas-chromatographic examination had been converted after a total reaction time of 9 hours into 2-methyl hexanol (58%), n-heptanol (37%) and hexane (5%).

EXAMPLE 31

62.5 ml of hexene-1 as well as 441,8 g $RhCl(CO)\{S[(CH_2)_3Si(OCH_3)_3]_2\}_2$, produced by reaction of $[Rh(CO)_2Cl]_2$ with $S[(CH_2)_3Si(OCH_3)_3]_2$ analogously to example 5, were dissolved in 180 ml of toluene and exposed to an $H_2/CO$ cold pressure (1:1) of 200 bar. At a temperature of 100° C., about 99% of the hexene-1 were converted within 10 minutes into the isomeric aldehydes. The isomer distribution was found gas-chromatographically at about 53% n-heptanal and 47% 2-methyl hexanal.

EXAMPLE 32

The solid substance treated according to example 24 was used for the hydrogenation of acrylic acid ethyl ester. In this regard, 68 mg of this catalyst were united with 8.70 ml of acrylic acid ethyl ester in a 50 ml flask, which was connected with a hydrogenation apparatus. While stirring magnetically, at a hydrogen pressure of about 1 bar and a temperature of 80° C.±2° C., the acrylic acid ethyl ester used was converted within 230 minutes quantitatively into propionic acid ethyl ester, as was determined on the basis of the absorbed quantity of hydrogen and of the gas chromatographic examination of the reaction product. The average $H_2$ absorption in this case amounted to 8.4 ml/min. Subsequently, first 4.35 ml of acrylic acid ethyl ester and, always after the conversion had taken place in 4.35 ml charges (40 m Mole) additional acrylic acid ethyl ester was added by spraying, in order to examine the activity of the catalyst in dependence on the level of filling of the piston, and simultaneously examine its shelf-life. The subsequent table presents an overall view of the conversion times required thereby and the average $H_2$-absorption time per minute, observed.

| Hydrogenation | Average $H_2$-absorption speed (ml/min) | Conversion time (min) |
|---|---|---|
| 2 | 8.8 | 110 |
| 3 | 12.1 | 79 |
| 4 | 14.2 | 68 |
| 5 | 16.5 | 59 |
| 6 | 14.6 | 66 |

According to this hydrogenation series, the catalyst was filtered off the clear, colorless solution, was washed with 2×10 ml of toluene, was dried at 100° C./$10^{-2}$ mbar and was used for a second hydrogenation series according to the same pattern. At the same time, it was possible to reproduce the data found in the first series. After the quantitative hydrogenation of 0.6 Mole acrylic acid ethyl ester to propionic acid ethyl ester these experiments were discontinued, without any desactivation of the used catalyst being observed.

EXAMPLE 33

The solution of 1.722 g of crotonic acid was reacted with 823 mg of the catalyst, treated according to example 26, and the 50 ml flask used, was connected to a hydrogenation apparatus. The crotonic acid used was hydrogenated quantitatively to butyric acid within 110 minutes, as was determined on the basis of the used-up $H_2$ quantity (485 ml) and during the gas-chromatographic examination of the reaction solution, while stirring magnetically at a temperature of 80° C.±2° C. and a hydrogen pressure of about 1 bar.

Further variations of the invention will be apparent to those skilled in the art from the foregoing description and are intended to be encompassed by the claims appended hereto.

EXAMPLE 34

To a solution of 2.0 g (7.60 m Mole) $RhCl_3.3H_2O$ in 60 ml water free ethanol were added dropwise 5.98 g (16.68 mMole) of $S[(CH_2)_3Si(OCH_3)_3]_2$. Thereupon the reactants were heated under reflux for 3 hours. After completion of the reaction 5 ml of distilled water were added dropwise within 10 minutes to the reaction mixture, whereby at once a very voluminous orangecoloured precipitate was formed. The suspension was diluted with further 20 ml of ethanol and thereafter heated at boiling temperature for 2 hours. The solid product obtained was transferred to an extraction hull and extracted with ethanol for 4 hours. Thereafter the product was dried at 80° C./10$^{-1}$ mbar. The yield amounted to 5.2 g (98.7% of the theoretical yield).

| Analyses: | % Rh | % Cl | % S |
|---|---|---|---|
| Theory | 14.85 | 15.35 | 10.15 |
| Founds | 13.69 | 14.60 | 9.49 |

We claim:
1. A complex compound of rhodium, comprised of at least one sulfide of the general formula (1)

$$R_{3-x}^1(R^2O)_xSi—R^3—S—R^4—Si(OR^5)_yR_{3-y}^6 \quad (1)$$

coordinatively bound to the central atom, any free valencies are occupied by carbon monoxide, an olefin, amine, phosphine or nitrile and a required charge equalization is accomplished with chloride, bromide or iodide ion, an acetate, trifluoroacetate or trifluoro-propionate ion, complete or partial substitution of such anions by hydride ion, being optional whereby in formula (1)
- each of R$^1$ and R$^6$ is a straight-chain alkyl or branched alkyl with 1 to 5 C-atoms, a cyclo-alkyl with 5 to 8 C-atoms, benzyl or phenyl, or substituted benzyl or substituted phenyl with methyl, ethyl, propyl, methoxy, ethoxy, NO$_2$, halide or cyanide; chloride or bromide;
- R$^2$ and R$^5$ each is a straight-chain alkyl or branched alkyl with 1 to 5 C-atoms, cycloalkyl with 5 to 8 C-atoms, substituted or unsubstituted phenyl or benzyl group or the 2-methoxy or 2-ethoxy-ethyl group, whereby R$^2$ and R$^5$ have the same or a different meaning;
- R$^3$ and R$^4$ each is a straight-chain alkylene or branched alkylene with 1 to 10 C-atoms a phenylene or cycloalkylene group with 5 to 8 C-atoms, unsubstituted or substituted with a methyl, ethyl, propyl or iso-propyl; or a unit of the formula

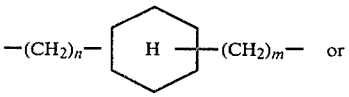 or

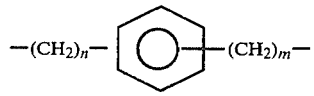

whereby n or m may be a number from 0 to 5 and H atoms in ring position may be substituted partly by halide, F, Cl, Br, or the cyanide group, and R$^3$ and R$^4$ have the same or a different meaning and whereby x and y may be 1, 2 or 3; but also 0, whenever R$^1$ R$^6$ is equal to chlorine or bromine, and x and y have the same or a different meaning.

2. A complex compound as in claim 1 of the stoichiometric formula:

RhX$_3$L$_3$ in which, as ligands L, sulfide compounds of the formula 1 are present and X is chloride, bromide, idodide, acetate, trifluoro acetate or trifluoro-propionate.

3. A complex compound which is obtained by treating the compound as defined in claim 2 with a solvent, such as benzene, toluene, xylene, n-hexane, cyclohexane, methylcyclohexane, monoglyme, diethylether tetrahydrofurane, dioxane or lower alcohols (1–5 carbons), in the presence of H$_2$ and CO at total pressures of 10 to 300 bar and temperatures of 50° to 200° C. and recovering the complex compound.

4. A complex compound as in claim 1 of the stoichiometric formula:

RhCl(CO)L$_2$ in which L is a ligand which is a sulfide compound of the formula (1).

5. A process for the production of complex compounds as defined in claim 2, wherein the sulfides of the general formula (1) are reacted with anhydrous rhodium compounds being salts of a halogen acid or of a lower organic carboxylic acid (1 to 5 carbon atoms) or bearing easily displaceable ligands.

6. The process as defined in claim 2 wherein the ligand is low aliphatic nitriles or benzonitrile.

7. A process as in claim 5, wherein the complex compound produced thereby is after-treated in a solvent with hydrogen and carbon monoxide at total pressures of about 10 to 300 bar and temperatures of 50° to 200° C.

8. The process as defined in claim 7, wherein the solvent is benzene, toluene, xylene, n-hexane, cyclohexane, methylcyclohexane, monoglyme, diethyl ether, tetrahydrofurane, dioxane or low alcohols.

9. A process for the production of the complex compounds as defined in claim 4, wherein the sulfide of the general formula (1) is reacted with [Rh(CO)$_2$Cl]$_2$ at a temperature below 100° C.

10. A polymer which is slightly soluble in organic solvents, with a silicic acid-like structure and the function of a rhodium carrier, to which rhodium salts of a halogen acid, or of a lower organic carboxylic acid, containing carbon monoxide, olefine, amine, phosphine or nitrile ligands or crystal water, are coordinatively bound by way of at least one ligand L$^1$,
- whereby L$^1$ signifies a sulfide compound L with trifunctionally substituted silicon of the formula:

$$R_{3-x}^1(R^2O)_xSi—R^3—S—R^4—Si(OR^5)_yR_{3-y}^6$$

in which the rhodium: sulfide ratio ranges from 1:1 to 1:10$^6$,
obtained from complex compounds of the stoichiometric compound RhX$_3$L$_3$ in which L represents at least one ligand of the formula (1) and carbon monoxide, olefine, amine, phosphine or nitrile or crystal water bound to any free coordination places and X, is chloride, bromide, iodide, acetate, trifluorocetate, or trifluoropropionate,
are reacted with water or an aqueous acid solution while distilling off of developing alcohol, or phenol.

11. A polymer as defined in claim 10 wherein said reaction takes place in the presence of excess sulfide beyond the stoichiometric compound RhX$_3$L$_3$.

12. A polymer as defined in claim 10 wherein said reaction takes place in the presence of cross-linking agents.

13. A polymer as defined in claim 11 wherein said reaction takes place in the presence of cross-linking agents.

14. A polymer as defined in claims 12 and 13 wherein said cross-linking agent is methyl silicate or ethyl silicate.

15. A polymer which is slightly soluble in organic solvents, with a silicic acid-like structure and the function of a rhodium carrier, to which rhodium salts of a halogen acid, or of a lower organic carboxylic acid, containing carbon monoxide, olefine, amine, phosphine or nitrile ligands or crystal water, are coordinatively bound by way of at least one ligand $L^1$.

whereby $L^1$ signifies a sulfide compound L with trifunctionally substituted silicon of the formula: (1)

$$R_{3-x}{}^1(R^2O)_x Si\text{---}R^3\text{---}S\text{---}R^4\text{---}Si(OR^5)_y R_{3-y}{}^6$$

in which the groups $OR^2$, $OR^5$, $R^1$ and $R^6$, present originally, are at least partially split off hydrolytically as alcohol, phenol, HCl or HBr, and in which the rhodium:sulfide ratio ranges from 1:1 to $1:10^6$, obtained by reacting the ligand L of the formula (1) with carbon monoxide, olefine, amine, phosphine or nitrile, or crystal water to any free coordination places, with water or an aqueous acid solution while distilling off of developing alcohol or phenol, and the solid matter formed is reacted with rhodium compounds, in the form of aqueous or anhydrous salts of a halogen acid or of a lower carboxylic acid, or in the form of rhodium compounds containing easily displaceable ligands, or with the compound $[Rh(CO)_2Cl]_2$.

16. A process for the production of a polymer as defined in claim 10, wherein a complex compound of the stoichiometric composition $RhX_3L_3$, in which L represents at least one ligand of the formula (1), provided with trifunctionally substituted silicon and carbon monoxide, olefine, amine, phosphine or nitrile, or crystal water to any free coordination places, and X is chloride, bromide, iodide, acetate, trifluoroacetate or trifluoropropionate, is reacted with water or an aqueous acid solution while distilling off of developing alcohol or phenol.

17. The process of claim 16 wherein the reaction is carried out in the presence of an excess of the sulfide L beyond the stoichiometric compound $RhX_3L_3$.

18. The process of claim 16 wherein the reaction is carried out in the presence of cross-linking agents.

19. A process for the production of a polymer as defined in claim 15, wherein at least one ligand of the formula (1), provided with trifunctionally substituted silicon and carbon monoxide, olefine, amine, phosphine or nitrile or crystal water, bound to still possibly free coordination places, and X is chloride, bromide, iodide, acetate, trifluoroacetate or trifluoropriopionate is reacted with water or an aqueous acid solution while distilling off of developing alcohol or phenol, and the solid matter formed thereby is reacted with rhodium compounds in the form of aqueous or anhydrous salts of a halogen acid or of a lower carboxylic acid, or rhodium compounds carrying easily displaceable ligands, or with the compound $[Rh(CO)_2Cl]_2$.

20. The process as defined in claim 9 wherein the reaction is carried out in the presence of cross-linking agents.

21. The process as defined in claim 20 wherein the reactive cross-linking agent is methyl or ethyl silicate.

22. A process as in claim 19, wherein a rhodium compound from the series $RhCl_3.3H_2O$; $RhBr_32H_2O$; $RhI_3$; $RhCl_3(CH_3CN)_3$; $RhCl_3(C_2H_5CN)_3$; $RhCl_3(C_6H_5CN)_3$; $RhBr_3(CH_3CH)_3$ or other rhodium systems, which carry easily substitutable ligands, is reacted with the desired quantity of sulfide compound L of formula (1) to form the complex compound $RhX_3L_3$ thereafter hydrolizing said complex compound with water or an aqueous acid solution, while distilling off of developing alcohol or phenol, and precipitating the solid product.

23. The process as defined in claim 22, wherein said reaction is carried out in a solution where the solvent is changed prior to hydrolysis to thereby avoid a reverse reaction.

24. A rhodium complex compound bound by way of inorganic carriers, and showing surface-positioned oxygen atoms having the formula:

$$RhX_3L_3 \text{ or } RhCl(CO)L_2,$$

wherein X is chloride, bromide, iodide, acetate, trifluoroacetate or trifluoropropionate and L represents at least one ligand of the formula (1)

$$R_{d-x}{}^1(R^2O)_x Si\text{---}R^3\text{---}S\text{---}R^4\text{---}Si(OR^5)_y R_{3-y}{}^6$$

and carbon monoxide, olefin, amine, phosphine or nitrile, or crystal water bound to any free coordination places, the bond to the carrier is established by reaction of the acid hydrogen with the $OR^2$, $OR^5$, $R^1$ and $R^2$ groups present, while alcohol, phenol, HCl or HBr is distilled off, wherein any uncoordinated radicals of the sulfide are bound on the carrier and the rhodium: sulfide ratio ranges from 1:1 to $1:10^3$;

said rhodium complex being obtained from a solution of the compound $RhX_3L_3$ or $RhCl(CO)L_2$, which is treated within the scope of the quantitative limit ratios provided with a suspension of the carrier material in an inert organic solvent at temperatures between room temperature and the reflux temperature of the suspension agent used.

25. The rhodium complex compound of claim 24, wherein said complex is obtained from said solution in the presence of excess sulfide L of formula (1).

26. A rhodium complex compound bound by way of inorganic carriers, and showing surface-positioned oxygen atoms having the formula:

$$RhX_3L_3 \text{ or } RhCl(CO)L_2,$$

wherein X is chloride, bromide, iodide, acetate, trifluoroacetate or trifluoropropionate and L represents at least one ligand of the formula (1)

$$R_{3-x}{}^1(R^2O)_x Si\text{---}R^3\text{---}S\text{---}R^4\text{---}Si(OR^5)_y R_{3-y}{}^6$$

and carbon monoxide, olefin, amine, phosphine or nitrile, or crystal water bound to any free coordination places, the bond to the carrier is established by reaction of the acid hydrogen with the $OR^2$, $OR^5$, $R^1$ and $R^6$ groups present, while alcohol, phenol, HCl or HBr is distilled off, wherein any uncoordinated radicals of the sulfide are bound on the carrier and the rhodium:sulfide ratio ranges from 1:1 to $1:10^3$;

said rhodium complex being obtained by treating a sulfide of the formula (1) with a suspension of the carrier material in an inert organic solvent at the stated temperature conditions, and subsequently the solid substance formed thereby is reacted with rhodium compounds carrying easily displaceable ligands, and in the form of anhydrous or aqueous salts of a halogen acid or of a lower carboxylic acid, or with the compound $[Rh(CO)_2Cl]_2$.

27. A carrier-fixed rhodium complex compound as in claims 24 or 26, wherein the carrier is pyrogeneous or precipitated silicic acid, quartz, a silicate glass, silicagel, titanium dioxide, zirconium dioxide, a zeolite, aluminum oxide, kaolin, bauxite, diatomaceous earth, or another substance with acid OH-groups built up from oxide compounds of aluminum and silicon and salts or oxides of other metals.

28. A process as in claims 16 or 19, wherein the polymeric solid substance or the carrier-fixed rhodium complex compound is after-treated in single stage or multi stage at total pressure of about 10 to 300 bar and temperatures of 50° to 200° C.
   with hydrogen/carbon monoxide mixtures and/or with a reduction agent.

29. The process as defined in claim 28, wherein the reduction agent is formaldehyde, alkali or alkaline earth boro-hydride, hydrazine or aluminum alkyl.

30. The process as defined in claim 28, wherein the reaction is carried out in the presence of a solvent.

31. The process as defined in claim 30; wherein the solvent is benzene, toluene, xylene, n-hexane, cyclohexane, methylcyclohexane, monoglyme, diethyl ether, tetrahydrofurance, dioxane and especially lower alcohols.

32. In a reaction catalyzed by rhodium, the improvement which comprises employing as the catalyst the complex of claim 1, or the polymer of claim 10 or claim 15, or the complex of claim 24 or claim 26.

* * * * *